US010159401B2

(12) United States Patent
Yamaya

(10) Patent No.: US 10,159,401 B2
(45) Date of Patent: Dec. 25, 2018

(54) ASSIST DEVICE AND ENDOSCOPIC SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/489,821

(22) Filed: Apr. 18, 2017

(65) Prior Publication Data

US 2017/0215709 A1 Aug. 3, 2017

Related U.S. Application Data

(63) Continuation of application No. PCT/JP2015/080771, filed on Oct. 30, 2015.

(30) Foreign Application Priority Data

Dec. 10, 2014 (JP) .................................. 2014-250213

(51) Int. Cl.
  *A61B 1/00* (2006.01)
  *A61B 1/005* (2006.01)
  (Continued)

(52) U.S. Cl.
  CPC ........ *A61B 1/00147* (2013.01); *A61B 1/0051* (2013.01); *A61B 1/00091* (2013.01);
  (Continued)

(58) Field of Classification Search
  CPC ....... A61B 1/00147; A61B 1/018; A61B 1/06; A61B 1/00091; A61B 1/015;
  (Continued)

(56) References Cited

U.S. PATENT DOCUMENTS 5,335,851 A * 8/1994 Adaska ................. A47G 21/18
239/33
2005/0065399 A1 3/2005 Sasaki et al.

FOREIGN PATENT DOCUMENTS

JP H07-059730 A 3/1995
JP 2003-079564 A 3/2003
(Continued)

OTHER PUBLICATIONS

Translation of JP 2013198673, 23 pages.*
(Continued)

*Primary Examiner* — Timothy J Neal
(74) *Attorney, Agent, or Firm* — Scully, Scott, Murphy & Presser, P.C.

(57) ABSTRACT

An assist device includes: a connecting section communicatively connected to the channel; a holding section attached to an outer side of either the insertion section of the endoscope or an operation section connected to the insertion section; and a flexible section forming an insertion path through which the treatment instrument is inserted, and including an expansion-and-contraction section including a more deformable structure than any other parts in an entire length between one end and another end of the flexible section. The flexible section is connected to the connecting section at the one end and connected to the holding section at the another end.

11 Claims, 4 Drawing Sheets

(51) Int. Cl.
*A61B 1/015* (2006.01)
*A61B 1/018* (2006.01)
*A61B 1/06* (2006.01)
*H04N 5/225* (2006.01)
*G02B 23/24* (2006.01)

(52) U.S. Cl.
CPC ...... *A61B 1/00112* (2013.01); *A61B 1/00137* (2013.01); *A61B 1/015* (2013.01); *A61B 1/018* (2013.01); *A61B 1/06* (2013.01); *H04N 5/2256* (2013.01); *G02B 23/2461* (2013.01); *G02B 23/2484* (2013.01); *H04N 2005/2255* (2013.01)

(58) Field of Classification Search
CPC .............. A61B 1/0051; A61B 1/00112; H04N 5/2256; H04N 2005/2255; G02B 23/2461
See application file for complete search history.

(56) References Cited

FOREIGN PATENT DOCUMENTS

| | | |
|---|---|---|
| JP | 2005-058749 A | 3/2005 |
| JP | 2013-198673 A | 10/2013 |
| WO | WO 2013/065509 A1 | 5/2013 |

OTHER PUBLICATIONS

English translation of International Preliminary Report on Patentability dated Jun. 22, 2017 together with the Written Opinion received in related International Application No. PCT/JP2015/080771.

International Search Report dated Dec. 8, 2015 issued in PCT/JP2015/080771.

* cited by examiner

ASSIST DEVICE AND ENDOSCOPIC SYSTEM

CROSS-REFERENCE TO RELATED APPLICATIONS

This application is a Continuation Application of PCT Application No. PCT/JP2015/080771, filed Oct. 30, 2015 and based upon and claiming the benefit of priority from prior Japanese Patent Application No. 2014-250213, filed Dec. 10, 2014, the entire contents of all of which are incorporated herein by reference.

BACKGROUND OF THE INVENTION

1. Field of the Invention

The present invention relates to an assist device to be attached to an endoscope to assist operations of a treatment instrument, and to an endoscopic system including the assist device.

2. Description of the Related Art

A treatment instrument may be inserted into or drawn out of a channel of an endoscope by an assistant other than an operator of the endoscope. However, when a treatment is performed, inserting or drawing the treatment instrument into or from the channel by the operator alone is more efficient. For example, International Publication No. 2013-065509 discloses an assist device including an operation body that allows the operator alone to perform an operation of inserting or drawing a treatment instrument into or from a channel, that is, to perform a forward or backward operation. A fixing member of the assist device is attached (fixed) to a periphery of an insertion section of the endoscope.

BRIEF SUMMARY OF THE INVENTION

According to one aspect of the present invention, an assist device that assists movement of a treatment instrument relative to a channel of an endoscope, the treatment instrument including an insertion body to be inserted through the channel, and that includes: a flexible section that forms an insertion path through which the treatment instrument is inserted, and includes an expansion-and-contraction section including a more deformable structure than any other parts in an entire length of the flexible section to make the entire length adjustable; a connecting section that is provided in the flexible section and connectable to the endoscope to communicate the channel and the insertion path; and a holding section that is provided in the flexible section and holds a part of either the insertion section of the endoscope or an operation section connected to the insertion section, the part being reachable by the flexible section whose entire length is adjusted by the expansion-and-contraction section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
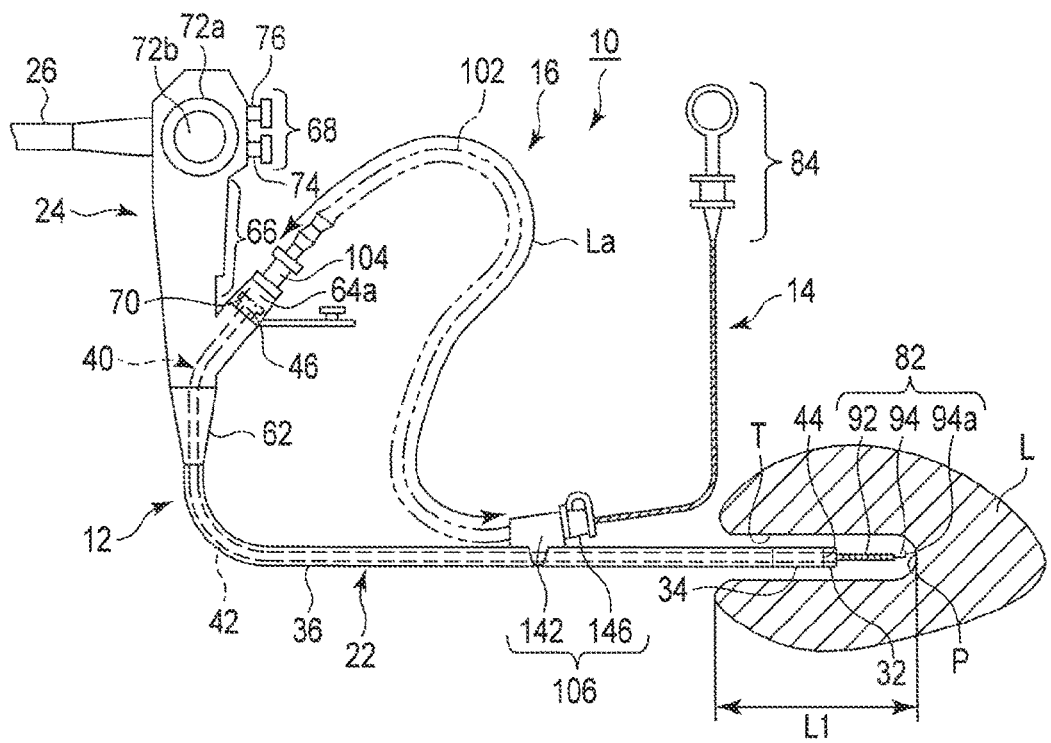
FIG. 1 is a schematic view of an endoscopic system according to a first embodiment, showing a state in which an assist device is attached to an endoscope, a treatment instrument is inserted through the assist device and a channel of the endoscope, and a holding section of the assist device is attached to a part of an insertion section of the endoscope near an entrance of a body cavity, while the insertion section is kept shallowly inserted in the body cavity.

Hereinafter, embodiments of this invention will be described with reference to the drawings.

A first embodiment will be described with reference to FIG. 1 to FIG. 4.

An endoscopic system (endoscope apparatus) 10 of the embodiment includes an endoscope 12, a treatment instrument 14, and an assist device 16. The treatment instrument 14 is movable relative to a channel 40 (to be described later) of the endoscope 12 for insertion of the treatment instrument. One end (a distal end) of the assist device 16 located at a position closer to a distal end of an insertion section 22 of the endoscope 12 is detachably fixed to the insertion section 22 or an operation section 24 of the endoscope 12, while another end (a proximal end) is detachably held by the operation section 24 of the endoscope 12. The assist device 16 is used to assist an operator in moving the treatment instrument 14, which includes an insertion body 82 (to be described later) inserted through the channel 40 of the endoscope 12, relative to the channel 40 (forward and backward movement and rotation). In other words, the assist device 16 assists the operator in moving the treatment instrument 14 extending from the one end of the assist device 16 relative to the endoscope 12.

Hereinafter, an example of holding an outside of the insertion section 22 with the distal end of the assist device 16 will be described. If the operation section 24 is held with the distal end of the assist device 16, it is preferable to hold a protection hood 62. For example, the operation section 24 may be held with the distal end of the assist device 16, if the entire length of the insertion section 22 is short.

A structure of the endoscope 12 will be briefly explained with reference to FIG. 1. The endoscope 12 may be of any conventional type that has the channel 40 (to be described later). As shown in FIG. 1, the endoscope 12 includes an elongated insertion section 22, the operation section 24 connected to a proximal end of the insertion section 22, and a universal cord 26 extending from a side portion of the operation section 24.

The insertion section 22 includes a hard distal formative section 32, a bending section 34 including a bendable bending tube formed of a plurality of bending pieces connected to one another (not shown), and a flexible tube section 36 that is freely bendable by external force, which are arranged in this order from the distal end side to the proximal end side of the insertion section 22.

A channel tube (treatment instrument insertion channel tube) 42 that forms the channel 40 for insertion of the treatment instrument is provided in the insertion section 22. A distal end 44 of the channel tube 42 is connected to a distal end opening 52 (to be described later) via the distal formative section 32. The channel 40 for insertion of the treatment instrument is preferably branched, for example, inside the operation section 24, as conventionally known. A first proximal end 46 of the channel 40 for insertion of the treatment instrument is connected to a hand side opening portion (plug connection pipe sleeve) 64a to be described later. A second proximal end (not shown) of the channel 40 for insertion of the treatment instrument is connected to a suction button 76 of a suction mechanism to be described later. A part of the channel 40 between the distal end opening 52 of the distal formative section 32 and a branch portion of the channel 40 for insertion of the treatment instrument is formed as a suction tube path as well as an insertion path through which the insertion body 82 of the treatment instrument 14 is inserted. The endoscope 12 of this embodiment does not necessarily comprise a suction mechanism.

Figure 2:
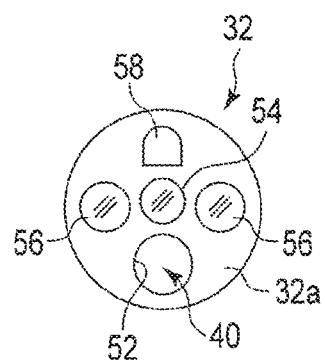
FIG. 2 is a schematic view of the endoscopic system according to the first embodiment, showing a distal face of a distal formative section of the insertion section of the endoscope.

As shown in FIG. 2, a distal end face 32a of the distal formative section 32 includes the distal end opening 52, an observation window 54, preferably two illumination windows 56 (one illumination window is acceptable), and a nozzle 58. As shown in FIG. 1, the distal end opening 52 communicates with a distal end of the channel tube 42, and forms a distal end of the channel 40. The observation window 54 constitutes a distal end of an observation optical system to observe an observation part. The illumination windows 56 constitute a distal end of an illumination optical system to illuminate the observation part. The nozzle 58 may eject gas and liquid through an ejection port (not shown) directed toward the observation window 54. The ejection of gas and liquid is controlled by a gas and water supply button 74 to be described later.

As shown in FIG. 1, the operation section 24 includes the protection hood 62, a treatment instrument introduction section 64, a grip portion 66, and an operation section main body 68, which are arranged in this order from the distal end side to the proximal end side. Preferably, the treatment instrument introduction section 64, the grip section 66, and the operation section main body 68 are integrally formed as one unit. The protection hood 62 holds a proximal end of the flexible tube section 36 and prevents the proximal end of the flexible tube 36 of the insertion section 22 from bending.

The treatment instrument introduction section 64 includes the hand side opening portion (plug connection pipe sleeve) 64a connected to the first proximal end 46 of the channel tube 42. An assist device plug 70 is attached to the hand side opening portion 64a of the treatment instrument introduction section 64. The assist device plug 70 has a valve structure, which prevents a liquid flowing through the channel tube 42 toward the proximal end side from leaking out of the endoscope 12, in a state where the insertion body 82 of the treatment instrument 14 and a connecting section 104 (to be described later) of the assist device 16 are inserted in the assist device plug 70. The assist device plug 70 may be similar to a conventional forceps plug.

The grip section 66 is a part which the operator holds in one hand, for example, the left hand. The operation section main body 68 may control bending of the bending section 34. The universal cord 26 extends from a side portion of the operation section main body 68.

The operation section main body 68 includes bending control knobs 72a and 72b, the gas and water supply button 74, and the suction button 76. The bending control knobs 72a and 72b allow remote control of the operation of bending the bending section 34. Generally, the operator operates the bending control knobs 72a and 72b with the thumb or the like of the left hand, while holding the grip section 66 with a palm of the left hand. A gas and water supply mechanism including the gas and water supply button 74 and the suction mechanism including the suction button 76 are conventionally known, and descriptions thereof are omitted.

The treatment instrument 14 includes the insertion body 82 that can be inserted through the channel 40 of the endoscope 12, and a base section (operation section) 84 disposed at a proximal end of the insertion body 82. The insertion body 82 is longer than the entire length of the channel 40, and may be, for example, several times as long. The distal end of the insertion body 82 may be inserted in and projected from the distal formative section 32 of the insertion section 22 through the channel 40 of the endoscope 12.

The insertion body 82 includes a sheath 92, and a wire 94 including an end effector 94a at its distal end. The sheath 92 may be formed of a mere resin tube having insulating properties or, for example, a coil sheath. The material of the sheath 92 is selected depending on the end effector 94a. The wire 94 is flexible.

The end effector 94a may have an appropriate shape, such as an L shape, a snare shape, or a basket shape. The end effector 94a can perform appropriate treatment using high-frequency energy for a living tissue sandwiched between the end effector 94a and a return electrode (not shown) attached to a patient.

The base section 84 includes a conventional slider mechanism. The wire 94 is movable in its axial direction relative to the sheath 92 by operation of the slider mechanism in the base section 84. Therefore, the wire 94 can be moved by the slider mechanism forward and backward in the axial direction of the insertion body 82 relative to the sheath 92. Furthermore, the insertion body 82, i.e. the sheath 92 and the wire 94, can be held by the operator, and rotated or revolved together around the axis of the insertion body 82.

The assist device 16 that is used to move the treatment instrument 14 relative to the channel 40 of the endoscope 12, for example, to advance, retract, and rotate the treatment instrument 14, will be described with reference to FIG. 1, FIG. 3A, and FIG. 3B.

The assist device 16 includes a long flexible section 102, the connecting section 104 configured to detachably connect a proximal end (connecting end) of the flexible section 102 to the hand side opening portion 64a of the endoscope 12, and a holding section 106 that holds an outside of the insertion section 22 of the endoscope 12 at a distal end (movable end) of the flexible section 102.

Preferably, the flexible section 102 is formed of a tube, which is easily bendable, resistant to breakage, and easily slidable relative to the insertion body 82 of the treatment instrument 14. The flexible section 102 is formed of, but not limited to, for example, a fluorine-based resin tube. The entire length of the flexible section 102 is shorter than the entire length of the treatment instrument 14, but preferably 500 mm or longer in practical use.

The flexible section 102 at least partly includes an expansion-and-contraction section 112 that may adjust the entire length of the flexible section 102. The expansion-and-contraction section 112 has a more deformable structure than the other part of the entire flexible section 102. Hereinafter, the expansion-and-contraction section 112 is explained as including a tube of a bellows structure. The expansion-and-contraction section 112 of the bellows structure preferably has a round cross section, but may have any other shape. A minimum inside diameter of the expansion-and-contraction section 112 is slightly larger than an outside diameter of the insertion body 82 of the treatment instrument 14. Preferably, the bellows-like expansion-and-contraction section 112 is not deformable by gravity or the like, but is shape-maintainable. Thus, the expansion-and-contraction section 112 includes a maintaining structure that deforms the expansion-and-contraction section 112 with force of a hand of the operator or assistant, and maintains a shape of the expansion-and-contraction section 112, that is, a desired length of an insertion path 130, when the expansion-and-contraction section 112 is extended or retracted. The maintaining structure of the expansion-and-contraction section 112 is attained by selecting a suitable material or adjusting the thickness or the like of the material. The shape of the expansion-and-contraction section 112 is normally maintained; however, the expansion-and-contraction section 112 has flexibility that easily deforms its shape by external force.

The flexible section 102 includes a distal end 102a and another end 102b respectively including a pipe sleeve 122 and a pipe sleeve 124. The pipe sleeve 122 at the distal end side is connected to the holding section 106.

The pipe sleeve 124 at the proximal end side is connected to the connecting section 104. In FIG. 3A, the distal end 102a of the flexible section 102 is in contact with the holding section 106. However, the distal end 102a may be separated from the holding section 106 via the pipe sleeve 122 at the distal end side. Therefore, the holding section 106 may be attached to a part near the distal end of the flexible section 102. In FIG. 3A, the proximal end 102b of the flexible section 102 is in contact with the connecting section 104. However, it is acceptable to separate the proximal end 102b from the connecting section 104 via the pipe sleeve 124 at the proximal end side. Therefore, the connecting section 104 may be attached to a part near the proximal end of the flexible section 102.

In the assist device 16, the flexible section 102, the connecting section 104, and the holding section 106 form the insertion path 130. The insertion path 130 is formed over the entire length of the assist device 16, and the insertion body 82 of the treatment instrument 14 is inserted through the path.

The connecting section 104 includes a connecting pipe sleeve 132 that has a proximal side opening end 132a of the insertion path 130. The connecting pipe sleeve 132 is connected to the assist device plug 70, while maintaining the state of opening the valve structure of the assist device plug 70 at the proximal side opening end 132a. Thus, in this embodiment, the connecting pipe sleeve 132 of the connecting section 104 is inserted in and engaged with a recess (not shown) of the assist device plug 70 made of an elastic member attached to the hand side opening portion 64a of the endoscope 12. Therefore, the connecting section 104 of the treatment instrument 14 communicates with the channel 40 of the endoscope 12 via the assist device plug 70 of the hand side opening portion (plug-connected pipe sleeve) 64a of the endoscope 12. The connecting section 104 of the treatment instrument 14 is detachably connected to the assist device plug 70 attached to the hand side opening portion (plug connection pipe sleeve) 64a of the endoscope 12.

The holding section 106 includes a main body 142, a connection pipe sleeve 144 attached to the main body 142, and a treatment instrument plug 146. The connection pipe sleeve 144 is similar to the hand side opening portion (plug connection pipe sleeve) 64a of the endoscope 12, and is fixed to the main body 142. The treatment instrument plug 146 may be similar to a conventional forceps plug as well as the assist device plug 70 described above. Thus, because of the valve structure, the treatment instrument plug 146 can prevent body fluid in a body cavity, which flows back through the channel 40 in the endoscope 12 and the insertion path 130 of the assist device 16, from externally leaking. Furthermore, the treatment instrument plug 146, through which the insertion body 82 of the treatment instrument 14 is inserted, can prevent liquid such as body fluid flowing through the channel 40 in the endoscope 12 and the insertion path 130 of the assist device 16, from externally leaking.

The main body 142 of the holding section 106 is made of, for example, resin material. The main body 142 of the holding section 106 includes a base body 152 forming a proximal end portion of the insertion path 130, and a pair of arms 154 extending from the base body 152. A cut portion 156 is provided in a space between the arms 154. The pair of arms 154 are elastically deformed to temporarily widen the cut portion 156, so that the main body 142 of the holding section 106 can be easily attached to and detached from an outer surface of the insertion section 22, which is represented by a broken line. The holding section 106 can detachably hold the outer peripheral surface of the insertion section 22 with the base body 152 (a contact surface 156a to be described later) and the pair of arms 154.

The main body 142 of the holding section 106 can be detachably attached, but preferably secured with appropriate force, to the outer peripheral surface of the insertion section 22. The main body 142 of the holding section 106 is secured to the outer peripheral surface of the insertion section 22 with such force that the operator can appropriately move the arms 154 of the holding section 106 along and around the insertion section 22 with the thumb and the index finger of the right hand, while supporting the outer peripheral surface of the insertion section 22 with the ring finger and the little finger of the right hand. In short, the operator can change the position of the holding section 106 appropriately, while holding the insertion section 22 of the endoscope 12 with the right hand. Thus, the holding section 106 is movable relative to the outer periphery of the insertion section 22 of the endoscope 12. Therefore, the operator can adjust the position of the main body 142 of the holding section 106 to a suitable position while holding the outer peripheral surface of the insertion section 22 with the right hand.

Figure 4:
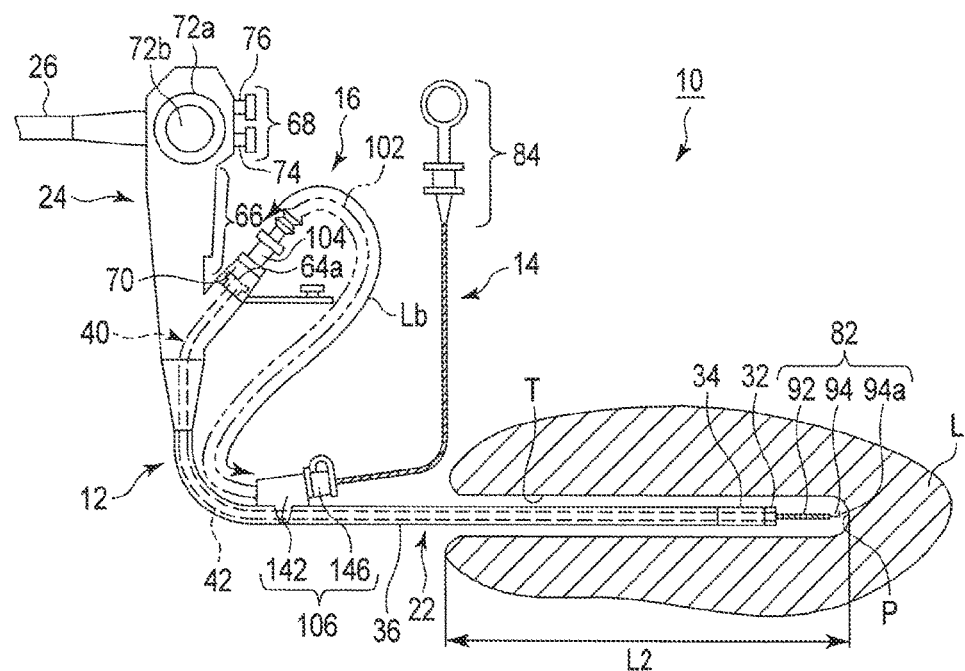
FIG. 4 is a schematic view of the endoscopic system according to the first embodiment, showing a state in which the assist device is attached to the endoscope, the treatment instrument is inserted through the assist device and the channel of the endoscope, and the holding section of the assist device is attached to a part of the insertion section of the endoscope near an entrance of the body cavity, while the insertion section is kept deeply inserted in the body cavity.

The base body 152 preferably has the contact surface 156a between the arms 154; the contact surface 156a is an inclined surface inclined relative to a longitudinal axis of the insertion path 130 in the base body 152. The contact surface 156a of the base body 152 detachably holds the outer peripheral surface of the insertion section 22 along with the pair of arms 154. When the holding section 106 is attached to the outer peripheral surface of the endoscope 12, the contact surface 156a of the base body 152 makes the treatment instrument plug 146 separate from the insertion section 22 of the endoscope 12, and brings the pipe sleeve 122 at the distal end side and the distal end 102a of the flexible section 102 close to the insertion section 22 of the endoscope 12. Thus, as shown in FIG. 1 and FIG. 4, the distal end 102a of the flexible section 102 can be close to the insertion section 22 of the endoscope 12.

The method for connecting the proximal side opening end 132a of the connecting section 104 and the hand side opening portion 64a of the endoscope 12 shown in FIG. 1 is not limited to the method described above. For example, the connection may be made by any structure that can detachably fix the connecting section 104 directly to the hand side opening portion 64a so as not to leak liquid without using the assist device plug 70. For example, the connecting section 104 may be made of an elastic member of silicone rubber, not a resin material. In this case, a watertight structure can be obtained by fitting the connecting section 104 directly to the end of the hand side opening portion 64a of the endoscope 12. Furthermore, the assist device 16 may not necessarily be provided with the connecting section 104. In this case, the pipe sleeve 124 at the proximal end side at the proximal end 102b of the flexible section 102 may be inserted in the channel 40 for insertion of the treatment instrument through the assist device plug 70, so that the proximal end of the assist device 16 can be secured to the endoscope 12.

Functions of the endoscopic system 10 having configurations as described above will be explained with reference to FIG. 1 and FIG. 4. A brief explanation will be given below for a case of endoscopic submucosal dissection (ESD), in which a layer below a pathological lesion P is filled with a liquid, such as physiological saline, and a periphery of the pathological lesion P is cut out by an electrosurgical knife.

The operator holds the grip section 66 of the operation section 24 of the endoscope 12 with the left hand, and the peripheral surface of the insertion section 22 with the right hand. While observing an observation image displayed on a monitor (not shown) via the observation optical system of the endoscope 12, the operator inserts the distal formative section 32 at the distal end of the insertion section 22 through an opening of a lumen (body cavity) T as a tubular path (tubular hole) of a living tissue L toward the pathological lesion P. At this time, the operator holds the grip section 66 of the operation section 24 of the endoscope 12 and suitably operates the bending control knobs 72a and 72b with the left hand, while pushing, pulling, and twisting the insertion section 22 with the right hand. Then, the operator moves the distal formative section 32 of the insertion section 22 near the pathological lesion P with an appropriate distance.

While the operator is holding the insertion section 22 of the endoscope 12 with the right hand and maintains the positional relationship between the pathological lesion P and the distal end face 32a of the distal formative section 32 of the insertion section 22, an assistant (another operator) attaches the connecting section 104 of the proximal end of the assist device 16 to the hand side opening portion (plug connection pipe sleeve) 64a of the endoscope 12.

As a result of attaching the proximal end of the assist device 16 to the endoscope 12, the insertion port of the channel 40 (treatment instrument plug 146) through which the distal end of the insertion body 82 of the treatment instrument 14 is inserted via the assist device 16 can be changed from the hand side opening portion (plug connection pipe sleeve) 64a of the operation section 24 to a position near the outer surface of the insertion section 22. Although the treatment instrument plug 146 is located near the outer surface of the insertion section 22, it is separated from the outer surface of the insertion section 22 by the contact surface 156a, so that the assistant can easily insert the end effector 94a at the distal end of the insertion body 82 through the insertion path 130, because the operator operates the insertion body 82 of the treatment instrument 14 inserted by the assistant in the insertion path 130.

At this time, the assistant appropriately adjusts the length of the expansion-and-contraction section 112 of the flexible section 102. Specifically, the assistant suitably extends the expansion-and-contraction section 112 of the flexible section 102 when attaching the holding section 106 to the insertion section 22. In other words, the assistant extends the length of the insertion path 130. Therefore, as shown in FIG. 1, when the distal end of the insertion section 22 is inserted to a part near the pathological lesion P, if the amount of insertion is small, that is, if the distance from the opening of the lumen T (the mouth or anus) to the pathological lesion P is short (distance L1), the assistant detachably attaches the holding section 106 to a reachable part of the insertion section 22 near the distal end. At this time, the expansion-and-contraction section 112 of the flexible section 102 may be extended to such an extent that no bend is formed in the flexible section 102 having a path length of, for example, La, and no bend is formed in the insertion body 82 of the treatment instrument 14.

Thereafter, the assistant inserts the insertion body 82 of the treatment instrument 14 through the insertion path 130 of the assist device 16 and the channel 40 of the endoscope 12, and locates the end effector 94a near the distal formative section 32 of the insertion section 22 of the endoscope 12. Then, the assistant arranges the holding section 106 of the assist device 16 to the outer peripheral surface of the insertion section 22 of the endoscope 12.

The operator moves the right hand to hold the holding section 106 with the palm, the middle finger, the ring finger, and the little finger of the right hand while maintaining the direction and position of the distal formative section 32 of the insertion section 22 of the endoscope 12, and also to hold the insertion body 82 of the treatment instrument 14 with the thumb and the index finger of the right hand. The middle finger of the right hand may hold either the holding section 106 or the insertion body 82 of the treatment instrument 14.

The assistant attaches the assist device 16 to the endoscope 12 preferably at a timing after the distal formative section 32 of the insertion section 22 of the endoscope 12 is placed in proximity to the pathological lesion P and the insertion position relative to the pathological lesion is determined. This is for the purpose of minimizing the movable range of the insertion body 82 necessary when the insertion body 82 of the treatment instrument 14 is held with the thumb and the index finger while the operator is grasping the insertion section 22 of the endoscope 12 together with the holding section 106. The maximum movable range of the insertion body 82 varies depending on the size or flexibility of joints of the right hand of the operator. The insertion body 82 of the treatment section 14 can be moved closer to and away from the holding section 106 by one operation within a range of about, for example, several centimeters.

The connecting section 104 at the proximal end of the assist device 16 that moves the treatment instrument 14 forward and backward is connected to the hand side opening portion 64a of the endoscope 12 via the assist device plug 70. The holding section 106 at the distal end of the assist device 16 is detachably attached to the insertion section 22 of the endoscope 12 of the pair of arms 154.

The position at which the holding section 106 on the distal end side of the assist device 16 is attached to the insert section 22 may be changed depending on the distance from the opening of the lumen T to the pathological lesion P. The operator can appropriately reposition and reattach the holding section 106 to an optimal position of the insertion section 22, while continuously holding the insertion section 22 of the endoscope 12 with the right hand.

As shown in FIG. 4, when the operator inserts the distal end of the insertion section 22 to a part near the pathological lesion P, if the amount of insertion is large, that is, if the distance from the opening of the lumen T to the pathological lesion P is long (distance L2), the operator or the assistant moves and attaches the holding section 106 to a part of the insertion section 22 closer to the proximal end. At this time, the assistant extends the expansion-and-contraction section 112 of the flexible section 102 to such an extent that no bend is formed in the flexible section 102 having a path length of, for example, Lb (<La), and no bend is formed in the insertion body 82 of the treatment instrument 14.

When the distal end of the insertion section 22 is inserted to a part near the pathological lesion P, if the amount of insertion is large, it is acceptable to detachably attach the holding section 106 to the protection hood 62, i.e., the operation section 24.

How the operator uses the right hand will be described more specifically. The insertion section 22 and the distal end of the assist device 16 are clamped and held by the palm and the three fingers of the middle finger, the ring finger, and the little finger, while the insertion body 82 of the treatment instrument 14 are pinched and held by the remaining two fingers of the thumb and the index finger. At this time, the operator moves the insertion body 82 of the treatment instrument 14 in the axial directions without releasing the right hand from the insertion section 22, thus making fine adjustment of forward and backward movements (approaching and removing operations) of the insertion body 82 in the axial direction about, for example, 10 mm relative to the holding section 106. Thus, while holding the insertion section 22 with the right hand, the operator can perform a precise manipulation of, for example, a high-frequency incision with the treatment instrument using high-frequency energy, by slightly changing the projection length of the end effector 94a of the treatment instrument 14 from the distal formative section 32 of the insertion section 22 of the endoscope 12.

The base section 84 of the treatment instrument 14 is generally operated by the assistant, not the operator of the endoscope 12, in accordance with the instructions of the operator. Output start and output stop of high-frequency energy can be generally performed by operating a foot switch by the operator.

The operator grasps the insertion section 22 with the palm and the three fingers of the middle finger, the ring finger, and the little finger of the right hand, while pinching and holding the insertion body 82 of the treatment instrument 14 by the thumb and the index finger, and rotates the insertion body 83 around the axis. Thus, the insertion body 82 can be rotated with respect to the channel 40. Therefore, the direction of the end effector 94a can be adjusted without changing the position and direction of the distal formative section 32 of the insertion section 22 of the endoscope 12.

In the ESD treatment, a plurality of treatment instruments 14 are replaced and inserted one after another in the assist device 16 and the channel 40 of the endoscope 12. The replacement is carried out not by the operator who is holding the insertion section 22 of the endoscope, but by the assistant (another operator).

The assist device 16 is cleaned, disinfected, and sterilized and then can be reused.

As described above, the endoscopic system 10 of this embodiment, in particular, the assist device 16, effects the following.

The length of the flexible section 102 of the assist device 16 is variable. For example, if a patient has pathological lesions P in both a shallow location as shown in FIG. 1 and a deep location as shown in FIG. 4, the treatment instrument 14 used in the case of FIG. 1 may be replaced with another one having a shorter length in the case of FIG. 4. If the length of the assist device is not variable as in the conventional art, the treatment instrument of the same length must be used in both cases, because the path length from the treatment instrument plug to the end face of the distal formative section of the insertion section is not variable. In general, a treatment instrument 14 with a shorter insertion body 82 has better distal-end following properties than a treatment instrument 14 with a longer insertion body 82. In this embodiment, the treatment instrument 14 with the comparatively long insertion body 82 is used in the treatment shown in FIG. 1, and the treatment instrument 14 with the insertion body 82 shorter than that used in the treatment shown in FIG. 1 can be used in the treatment shown in FIG. 4. Therefore, safer and more efficient treatment can be performed in the case of the treatment as shown in FIG. 4.

If the length of the flexible section is not variable as in the conventional assist device (or the variation range is limited to a deformable range of a cylindrical tube (for example, within about 1 mm)), the effective length of the treatment instrument must be the length from the distal end face 32a of the insertion section 22 of the endoscope 12 to the hand side opening portion 64a plus the total length of the assist device and the distance from the mouth side or anus side of the lumen T to the pathological lesion P. The assist device 16 of this embodiment includes the flexible section 102 including the bellows structure. Because of the flexible section 102, the length of the assist device 16 can be adjusted from the minimum length of, for example, about several hundreds of millimeters to about one meter according to circumstances. Thus, the use of the assist device 16 of this embodiment enables the use of treatment instruments 14 with insertion bodies 82 of a variety of lengths. Therefore, the use of the assist device 16 of this embodiment can increase options of applicable treatment instruments 14.

In particular, in the case where the pathological lesion P is located in a deep position from the mouth side or anus side of the lumen T (L2 is much longer than L1) as shown in FIG. 4, the position of attachment of the holding section 106 to the insertion section 22 is closer to the hand side opening portion 64a of the operation section 24. Therefore, the length of the assist device 16 can be short, which enables use of the treatment instrument 14 including a shorter insertion body 82 than that used for treatment of a shallow pathological lesion P shown in FIG. 1. The shorter the length of the treatment instrument 14, the better the distal-end following properties. Accordingly, the treatment of safer and shorter range can be performed, thereby reducing the burden on the patient.

With the assist device 16 that includes the flexible section 102 having the expansion-and-contraction section 112, the expansion-and-contraction section 112 can be elongated when the holding section 106 of the assist device 16 is attached to a distal end side of the insertion section 22, and can be shorter when the holding section 106 is attached to a proximal end side of the insertion section 22. Therefore, when the holding section 106 of the assist device 16 is suitably attached to the insertion section 22, the flexible section 102 is prevented from bending while the play of the flexible section 102 can be reduced. Accordingly, when the operator performs various treatments using the endoscopic system 10, the presence of the assist device 16 is unlikely to become obstructive.

Thus, this embodiment can provide the assist device 16 that maintains satisfactory operability regardless of to which part of the insertion section 22 of the endoscope 12 the assist device 16 is attached.

As described above, the use of the assist device 16 of this embodiment allows the operator to directly move forward or backward and to directly rotate the insertion body 82 of the treatment instrument 14 with the fingers of the right hand without releasing the right hand from the insertion section 22, that is, the use of the assist device 16 of this embodiment allows the operator to move the treatment instrument 14. With the assist device 16 of this embodiment, for example, the sophisticated ESD treatment that must move the treatment instrument 14 precisely can be carried out more accurate and safer in a short period of time. Therefore, the operator can efficiently complete the treatment in a short period of time. Accordingly, the assist device 16 of this embodiment can reduce the burden on the operator and further reduce the burden on the patient.

In this endoscopic system 10, the holding section 106 may be attached to the outer peripheral surface of the insertion section 22 immediately before starting treatment. Unlike the conventional assist device as disclosed in, for example, International Publication No. 2013/065509, the insertion body need not be inserted through a narrow holding mechanism in advance of the treatment. The holding section 106 can be arranged at an optimal position when treatment of the pathological lesion P is started, with the distal end face 32a of the distal formative section 32 of the insertion section 22 of the endoscope 12 facing the pathological lesion P.

Figure 3A:
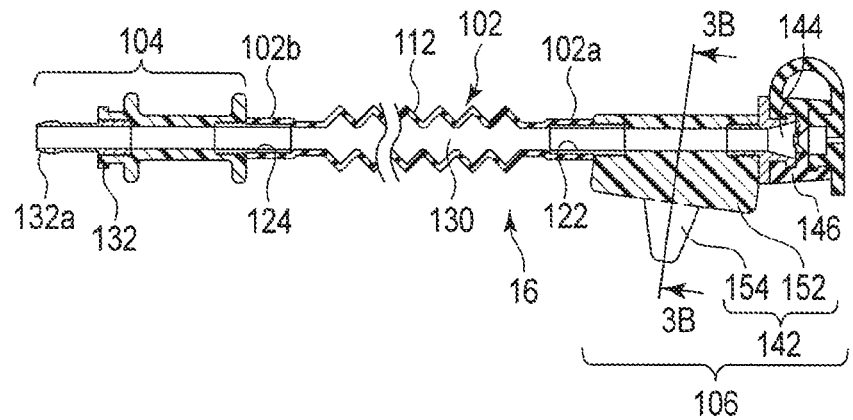
FIG. 3A is a longitudinal sectional view of the assist device of the endoscopic system according to the first embodiment.
Figure 3B:
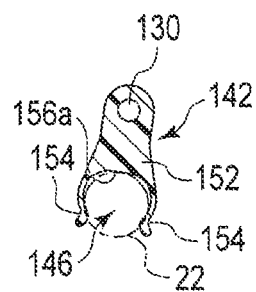
FIG. 3B is a cross-sectional view taken along line 3B-3B in FIG. 3A.

In the example shown in FIG. 3A and FIG. 3B, the base body 152 of the main body 142 of the holding section 106 of the assist device 16 and the pair of arms 154 are integrally formed of a plastic resin material as one unit. Besides, although not shown in the drawings, it is acceptable to form the base body 152 of the main body 142 of the holding section 106 of the assist device 16 of a plastic resin material, to form the pair of arms 154 and the contact surface 156a of a rubber material, and to integrate the resin part and the rubber part into one unit.

A first modification of the first embodiment is explained below with reference to FIG. 5.

The flexible section 102 is not limited to the structure shown in FIG. 3A, that is, the flexible section 102 does not necessarily include an expansion-and-contraction section 112 over the entire length. As shown in FIG. 5, the flexible section 102 includes an expansion-and-contraction section 112 and a cylindrical flexible body 114. The expansion-and-contraction section 112 comprises a first bellows body 112a including a bellows structure, and a second bellows body 112b including a bellows structure. The cylindrical flexible body 114 is interposed between the first and second bellows bodies 112a and 112b. The first bellows body 112a is arranged closer to the holding section 106, and the second bellows body 112b is arranged closer to the connecting section 104.

A pipe sleeve 116a is interposed between the first bellows body 112a and the flexible body 114, and a pipe sleeve 116b is interposed between the second bellows body 112b and the flexible body 114. The flexible body 114 is an elastic body; for example, a fluorine-based resin tube, a fluorine-based resin tube containing a blade to increase the flexural capacity, or a urethane-based resin tube which contains a blade, and an insertion path 130 of which in the flexible section 102 is coated with fluorine-based resin to facilitate the forward and backward movement in the axial direction of the insertion body 82 of the treatment instrument 14.

For example, the assistant can elongate and contract one or both of the first and second bellows bodies 112a and 112b. The operator can elongate and contract the first bellows body 112a with the palm or the like without releasing the right hand from the insertion section 22, while holding the insertion section 22 with, for example, the thumb and the index finger. Thus, the length of the flexible section 102 can be adjusted.

The lengths of the first and second bellows bodies 112a and 112b and the length of the flexible body 114 can be set to appropriate values. The first bellows body 112a may be longer or shorter than the second bellows body 112b. The first bellows body 112a may be longer or shorter than the flexible body 114. Similarly, the second bellows body 112b may be longer or shorter than the flexible body 114.

Figure 5:
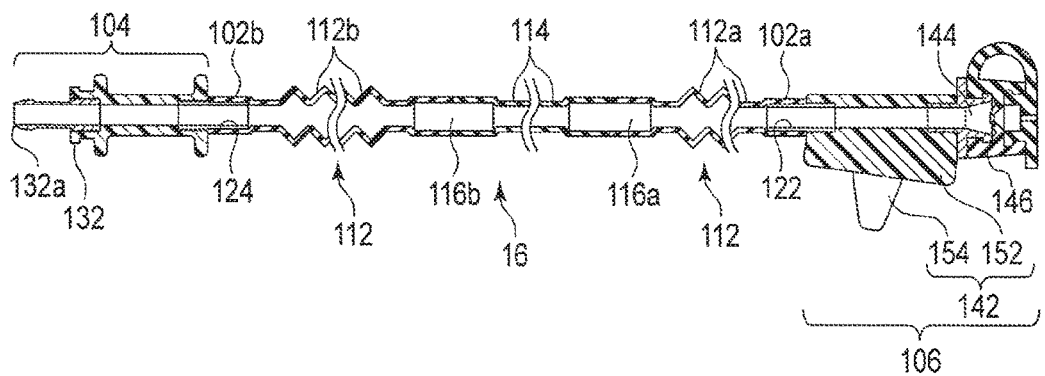
FIG. 5 is a longitudinal sectional view of an assist device of an endoscopic system according to a first modification of the first embodiment.

Each of the first and second bellows bodies 112a and 112b shown in FIG. 5 may be shorter than the expansion-and-contraction section 112 shown in FIG. 3A. Since the expansion-and-contraction section 112 and the flexible body 114 are separate, the part where the length of the flexible tube 102 is adjusted can be definite. For example, if the assistant adjusts the length of the flexible tube 102, force can be applied to a definite position, because the expansion-and-contraction section 112 and the flexible body 114 are separate. Therefore, when the assistant adjusts the length of the flexible tube 102 while the operator is holding the insertion section 22 and the holding section 106, in what manner force should be exerted on the flexible section 102 can be easily estimated.

In the example described above, the flexible body 114 is interposed between the first and second bellows bodies 112a and 112b. However, the arrangement of the flexible body 114 and the first and second bellows bodies 112a and 112b may be reversed. In other words, it is acceptable to form a bellows body as the expansion-and-contraction section 112 between flexible bodies.

A second modification of the first embodiment is explained below with reference to FIG. 6.

Figure 6:
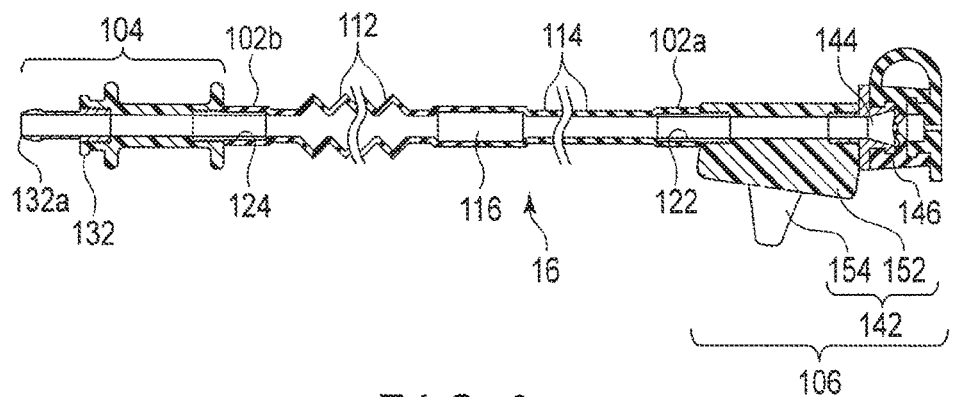
FIG. 6 is a longitudinal sectional view of an assist device of an endoscopic system according to a second modification of the first embodiment.

As shown in FIG. 6, a flexible section 102 includes an expansion-and-contraction section 112 of a bellows structure and a cylindrical flexible body 114. A pipe sleeve 116 is interposed between the expansion-and-contraction section 112 and the flexible body 114. The expansion-and-contraction section 112 is arranged closer to the holding section 106, and the flexible body 114 is arranged closer to the connecting section 104.

The assistant extends and contracts the expansion-and-contraction section 112, so that the length of the flexible section 102 can be appropriately adjusted.

A third modification of the first embodiment is explained below with reference to FIG. 7.

Figure 7:
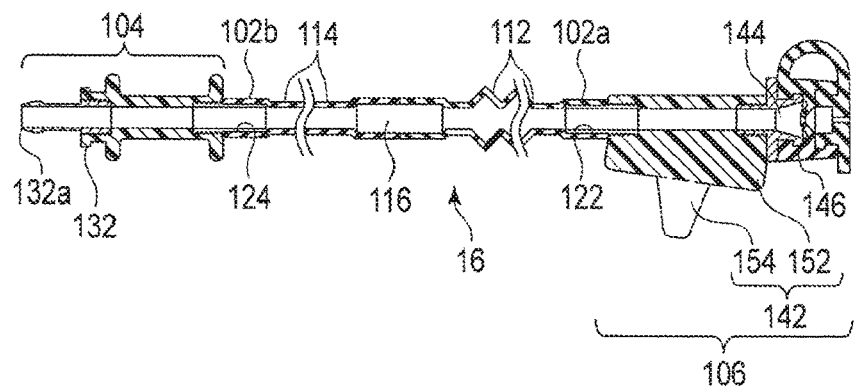
FIG. 7 is a longitudinal sectional view of an assist device of an endoscopic system according to a third modification of the first embodiment.

As shown in FIG. 7, a flexible section 102 includes an expansion-and-contraction section 112 of a bellows structure and a cylindrical flexible body 114. A pipe sleeve 116 is interposed between the expansion-and-contraction section 112 and the flexible body 114. The expansion-and-contraction section 112 is arranged closer to the connecting section 104, and the flexible body 114 is arranged closer to the holding section 106.

The assistant or the operator extends and contracts the expansion-and-contraction section 112, so that the length of the flexible section 102 can be appropriately adjusted.

The second embodiment will be explained below with reference to FIG. 8. This embodiment is a variation of the first embodiment including the modifications. The same members or the members having the same functions as those of the members of the first embodiment are identified by the same reference symbols as those used for the embodiment as much as possible, and detailed explanations thereof are omitted.

Figure 8:
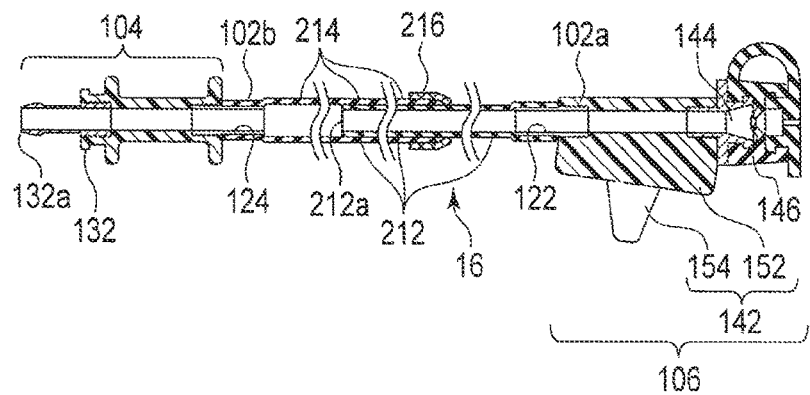
FIG. 8 is a longitudinal sectional view of an assist device of an endoscopic system according to a second embodiment.

As shown in FIG. 8, a flexible section 102 of this embodiment differs from the flexible section 102 of the first embodiment shown in FIG. 3A in that the former does not include a bellows structure. The flexible section 102 of this embodiment includes, as an expansion-and-contraction section, first and second flexible bodies 212 and 214 which are cylindrical. The first and second flexible bodies 212 and 214 have substantially equal lengths. A distal end of the first flexible body 212 is connected to a holding section 106 via a pipe sleeve 122. A proximal end of the second flexible body 214 is connected to a connecting section 104 via a pipe sleeve 124. An outer diameter of the first flexible body 212 and an inner diameter of the second flexible body 212 are determined to be such sizes that the bodies can slide on each other. In other words, an outer peripheral surface of the first flexible body 212 and an inner peripheral surface of the second flexible body 214 are formed to be slidable on each other.

A lock body (maintaining structure) 216 projecting radially inward is provided at a distal end of the second flexible body 214. The lock body 216 has a cylindrical shape. The lock body 216 is locked on the outer peripheral surface of the first flexible body 212, and can immovably lock the second flexible body 214 against gravity or the like. Thus, the lock body 216 maintains the shape of an expansion-and-contraction section 112 in association with the outer peripheral surface of the first flexible body 212. In other words, the lock body 216 functions as a part of the maintaining structure that maintains an insertion path 130 at a desirable length. Furthermore, the lock body 216 can function as a sealing member that prevents a fluid, such as a liquid or gas passing through the insertion path 130, from leaking out of the flexible section 102, in the state that the lock body 216 is locked on the outer peripheral surface of the first flexible body 212.

As the treatment proceeds, the path length of the flexible section 102 of the assist device 16 varies from the length La shown in FIG. 1 to the length Lb (<La) shown in FIG. 4. Accordingly, the length of the flexible tube 102 is generally reduced as the treatment proceeds. Therefore, the lock body 216 is preferably formed to cause friction force to act, in association with the outer peripheral surface of the first flexible body 212, so that a proximal end 212a of the first flexible body 212 may easily move close to, rather than away from, the connecting section 104.

When the assistant adjusts the length of the lock body 216, that is, adjusts the position of the outer peripheral surface of the first flexible body 212 relative to the lock body 216 of the second flexible body 214, the position of the outer peripheral surface of the first flexible body 212 relative to the lock body 216 of the second flexible body 214 can be moved by the assistant's operation. When the assistant has adjusted the flexible section 102 to an appropriate length, if the assistant releases the lock body 216 of the second flexible section 214 and the first flexible section 212, the lock body 216 can press the outer peripheral surface of the first flexible body 212. As a result, the first flexible body 212 can be positioned relative to the second flexible body 214.

When the connecting section 104 of the assist device 16 is attached to the hand side opening portion 64a and the holding section 106 is attached to the distal formative section 32 of the insertion section 22 of the endoscope 12, the proximal end 212a of the first flexible body 212 has a positional relation with the lock body 216 as shown in FIG. 8. Specifically, the assist device 16 has such a length that the first and second flexible bodies 212 and 214 may not be removed from each other even when the insertion path 130 is extended to the maximum length in use.

The assistant extends and contracts the first and second flexible bodies 212 and 214 formed as the expansion-and-contraction section, so that the length of the flexible section 102 can be appropriately adjusted.

The assist device 16 of this embodiment includes the flexible section 102 including a double tube of the first and second flexible bodies 212 and 214. Because of the flexible section 102, the length of assist device 16 can be adjusted from the minimum length of, for example, about several hundreds of millimeters to about one meter according to circumstances.

The assist device 16 can be used for endoscopic retrograde cholangiopancreatography (ERCP), if a side-viewing endoscope is used and an appropriate treatment instrument 14 is selected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assist device that assists movement of a treatment instrument relative to a channel of an insertion section of an endoscope, the treatment instrument including an insertion body to be inserted through the channel, the assist device comprising:

a connecting section that is configured to be connected to a proximal end of the channel of the endoscope and configured to be communicated with the channel;

a holding section that is configured to be attached to an outer side of either the insertion section of the endoscope or an operation section of the endoscope connected to the insertion section of the endoscope; and a flexible section that forms an insertion path through which the treatment instrument is inserted, the flexible section including an expansion-and-contraction section including a more deformable structure than any other parts in an entire length between one end and an other end of the flexible section, the flexible section being connected to the connecting section at the one end and connected to the holding section at the other end, wherein:

the holding section is detachably attached to either the insertion section or the operation section of the endoscope, and the expansion-and-contraction section is configured to be elongated in a state where the holding section is attached to a first position of a distal end side of the insertion section as compared with a state where the holding section is attached to a second position of a proximal end side of the insertion section with respect to the first position or where the holding section is attached to the operation section.

2. The assist device according to claim 1, wherein the holding section holds a part of either the insertion section or the operation section of the endoscope, the part being reachable by the flexible section whose entire length is adjusted by the expansion-and-contraction section.

3. The assist device according to claim 1, wherein the expansion-and-contraction section of the flexible section has flexibility and the flexible section includes a maintaining structure that maintains the flexible section to a desired length.

4. The assist device according to claim 1, wherein the expansion-and-contraction section of the flexible section includes a tube of a bellows structure.

5. The assist device according to claim 1, wherein the expansion-and-contraction section of the flexible section includes an elastic body.

6. The assist device according to claim 1, wherein:

the holding section is configured to be reattached to the insertion section, and a position at which the holding section is attached to the insertion section is configured to be changed depending on a distance from an opening of a lumen to a pathological lesion.

7. The assist device according to claim 1, wherein the flexible section is formed of a tube.

8. An endoscopic system comprising:

an endoscope including an insertion section with a channel;

a first treatment instrument including an insertion body; and an assist device that is connected to an end of the channel at the connecting section and that assists movement of the first treatment instrument relative to the channel of the insertion section of the endoscope, the assist device including:

a connecting section that is connected to a proximal end of the channel of the endoscope and configured to be communicated with the channel, a holding section that is configured to be attached to an outer side of either the insertion section of the endoscope or an operation section of the endoscope connected to the insertion section of the endoscope, and a flexible section that forms an insertion path through which the treatment instrument is inserted, the flexible section including an expansion-and-contraction section including a more deformable structure than any other parts in an entire length between one end and an other end of the flexible section, the flexible section being connected to the connecting section at the one end and connected to the holding section at the other end, wherein:

the first treatment instrument is configured to be inserted through the insertion path of the assist device and the channel of the endoscope, the holding section is detachably attached to either the insertion section or the operation section of the endoscope, and the expansion-and-contraction section is configured to be elongated in a state where the holding section is attached to a first position of a distal end side of the insertion section as compared with a state where the holding section is attached to a second position of a proximal end side of the insertion section with respect to the first position.

9. The endoscopic system according to claim 8, further comprising a second treatment instrument including an insertion body which has a length different from a length of the insertion body of the first treatment instrument and being configured to be inserted through the insertion path of the assist device and the channel of the endoscope.

10. The endoscopic system according to claim 8, wherein:

the holding section is configured to be reattached to the insertion section, and a position at which the holding section is attached to the insertion section is configured to be changed depending on a distance from an opening of a lumen to a pathological lesion.

11. The endoscopic system according to claim 8, wherein the flexible section is formed of a tube.

* * * * *